US009592279B2

(12) United States Patent
Matsuyama et al.

(10) Patent No.: US 9,592,279 B2
(45) Date of Patent: Mar. 14, 2017

(54) AGENT FOR NEUROPATHIC PAIN (71) Applicants: NATIONAL UNIVERSITY CORPORATION NAGOYA UNIVERSITY, Nagoya-shi, Aichi (JP); SEIKAGAKU CORPORATION, Tokyo (JP)

(72) Inventors: Yukihiro Matsuyama, Aichi (JP); Kenji Kadomatsu, Aichi (JP); Shiro Imagama, Aichi (JP); Akiomi Tanaka, Tokyo (JP)

(73) Assignees: NATIONAL UNIVERSITY CORPORATION NAGOYA UNIVERSITY, Nagoya-shi (JP); SEIKAGAKU CORPORATION, Tokyo (JP)

( * ) Notice: Subject to any disclaimer, the term of this patent is extended or adjusted under 35 U.S.C. 154(b) by 599 days.

(21) Appl. No.: 13/858,242

(22) Filed: Apr. 8, 2013

(65) Prior Publication Data
US 2013/0230509 A1  Sep. 5, 2013

Related U.S. Application Data (62) Division of application No. 12/937,456, filed as application No. PCT/JP2009/057503 on Apr. 14, 2009, now abandoned.

(30) Foreign Application Priority Data

Apr. 14, 2008 (JP) .................................. 2008-105183

(51) Int. Cl.
A61K 38/46 (2006.01)
A61K 38/48 (2006.01)
C12N 9/88 (2006.01)
A61K 38/51 (2006.01)
C12N 9/24 (2006.01)
C07D 471/10 (2006.01)

(52) U.S. Cl.
CPC ............ *A61K 38/51* (2013.01); *C07D 471/10* (2013.01); *C12N 9/2402* (2013.01); *C12Y 302/01096* (2013.01)

(58) Field of Classification Search
CPC .................. A61K 38/51; C07D 471/10; C12Y 302/01096
USPC .............................................. 424/94.5, 78.05
See application file for complete search history.

(56) References Cited

U.S. PATENT DOCUMENTS

2005/0118157 A1   6/2005  McMahon et al.
2005/0244399 A1  11/2005  English

2008/0025963 A1 *  1/2008  Gruskin .............. A61K 9/0019
                                                        424/94.6

FOREIGN PATENT DOCUMENTS

EP          1 911 460 A1       4/2008
JP          2005-526740        9/2005
WO     WO 2004/103299 A2      12/2004

OTHER PUBLICATIONS

Meyer et al. JHU APL tech digest 2005 26, pp. 56-66.*
Hulsebosch, Clarie E.; "From Discovery to Clinical Trials: Treatment Strategies for Central Neuropathic Pain after Spinal Cord Injury," Current Pharmaceutical Design, 2005, No. 11, pp. 1411-1420, XP002661812, ISSN: 1381-6128.
Barritt, A.W., et al.; "Chondroitinase ABC Promotes Sprouting of Intact and Injured Spinal systems after Spinal Cord Injury," The Journal of Neuroscience, Oct. 18, 2006, vol. 26, No. 42, pp. 10856-10867.
Bradbury, Elizabeth J., et al., "Chondrotinase ABC promotes functional recovery after spinal cord injury." Nature, vol. 416, Apr. 2002, pp. 636-640.
Tsuchihara, T. et al., "HGF gene therapy for neuropathic pain model in rats—Nonviral HVJ (hemagglutinating virus of Japan) liposome-mediated retrograde gene transfer—" (Shinkei Insei Totsu Model ni Taisuru HGF Idenshi Chiryo no Koka—HVJ Liposome-ho ni yoru Gyakkosei Shinkeinai Idenshi Donyu)—*Peripheral Nerve (Massho Shinkei)*, 2007, vol. 18, No. 2, p. 236.
International Search Report for International Application No. PCT/JP09/057503 dated May 14, 2009.
Bonnington et al., Signalling pathways involved in the sensitisation of mouse nociceptive neurones by nerve growth factor, J Physiol (2003), 551.2, pp. 433-446.
Dyck et al., Intradermal recombinant human nerve growth factor induces pressure allodynia and lowered heat-pain threshold in humans, Neurology (1997); 48:501-505.
Lewin et al., Peripheral and Central Mechanisms of NGF-induced Hyperalgesia, European Journal of Neuroscience (1994), vol. 6, pp. 1903-1912.
Ruiz et al., Behavioral and histological effects of endoneurial administration of nerve growth factor: possible implications in neuropathic pain, Brain Research 1011 (2004) 1-6.
Svensson et al., Injection of nerve growth factor into human masseter muscle evokes long-lasting mechanical allodynia and hyperalgesia, Pain 104 (2003) 241-247.
Supplementary European Search Report dated Oct. 31, 2011, regarding Application No. 09732985.8.

(Continued)

*Primary Examiner* — Md. Younus Meah
(74) *Attorney, Agent, or Firm* — Kratz, Quintos & Hanson, LLP (57) ABSTRACT An object of the present invention is to provide a substance which can be used as an active ingredient for improving neuropathic pain having a mechanism of action different from those of currently available agents and, therefore, provide an improving agent for neuropathic pain which rarely interacts with currently available agents and also does not have adverse reactions similar to those of currently available agents. An improving agent for neuropathic pain due to a hyperalgesic response of the present invention for resolution is characterized by comprising, as an active ingredient, a lyase (an elimination enzyme) which has an activity of degrading a chondroitin sulfate chain of a chondroitin sulfate proteoglycan, and is typified by chondroitinase ABC which selectively removes chondroitin sulfate and dermatan sulfate of a proteoglycan.

12 Claims, 4 Drawing Sheets

(56) References Cited

OTHER PUBLICATIONS

Hulsebosch, Claire E.; "From Discovery to Clinical Trials: Treatment Strategies for Central Neuropathic Pain after Spinal Cord Injury," Current Pharmaceutical Design, 2005, No. 11, pp. 1411-1420, XP002661812, ISSN: 1381-6128.

* cited by examiner

Fig.1

** $p<0.01$ ; Significant difference by t-test as compared with group with administration of physiological saline

Fig.2

$p<0.01$, * $p<0.001$ : Significant difference by t-test as compared with group with administration of physiological saline

Fig.3

\### p<0.001 ; Significant difference by t-test as compared with sham group
\* p<0.05 : Significant difference by t-test as compared with group with administration of physiological saline

Fig.4

\* p<0.05, \*\* p<0.01 : Significant difference by Wilcoxon rank sum test as compared with group with administration of physiological saline

Fig.5

\* p<0.05, \*\* p<0.01 ; Significant difference by t-test as compared with group with administration of physiological saline

Fig.6

\*\* p<0.01, \*\*\* p<0.001 ; Significant difference by t-test as compared with group with administration of physiological saline

Fig.7 p<0.001 ; Significant difference by t-test as compared with sham group
* p<0.05 ; Significant difference by t-test as compared with group with administration of physiological saline

SEQUENCE LISTING

<160> NUMBER OF SEQ ID NOS: 2

<210> SEQ ID NO 1
<211> LENGTH: 1021
<212> TYPE: PRT
<213> ORGANISM: Proteus vulgaris

<400> SEQUENCE: 1

```
Met Pro Ile Phe Arg Phe Thr Ala Leu Ala Met Thr Leu Gly Leu Leu
1               5                   10                  15

Ser Ala Pro Tyr Asn Ala Met Ala Thr Ser Asn Pro Ala Phe Asp
            20                  25                  30

Pro Lys Asn Leu Met Gln Ser Glu Ile Tyr His Phe Ala Gln Asn Asn
                35                  40                  45

Pro Leu Ala Asp Phe Ser Ser Asp Lys Asn Ser Ile Leu Thr Leu Ser
    50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
                100                 105                 110

Phe Trp Leu Tyr Asn Glu Lys Pro Ile Asp Gly Tyr Leu Thr Ile Asp
                115                 120                 125

Phe Gly Glu Lys Leu Ile Ser Thr Ser Glu Ala Gln Ala Gly Phe Lys
            130                 135                 140

Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
                165                 170                 175

Ser Asp Gly Thr Gln Asp Ser Ile Gly Arg Ser Leu Gly Ala Lys Val
                180                 185                 190

Asp Ser Ile Arg Phe Lys Ala Pro Ser Asn Val Ser Gln Gly Glu Ile
            195                 200                 205

Tyr Ile Asp Arg Ile Met Phe Ser Val Asp Ala Arg Tyr Gln Trp
    210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
        290                 295                 300

Gly Arg His Leu Ile Thr Asp Lys Gln Ile Ile Ile Tyr Gln Pro Glu
305                 310                 315                 320

Asn Leu Asn Ser Gln Asp Lys Gln Leu Phe Asp Asn Tyr Val Ile Leu
        325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365
```

-continued

```
Met Thr Lys His Leu Leu Asp Gln Gly Phe Val Lys Gly Ser Ala Leu
    370             375             380

Val Thr Thr His His Trp Gly Tyr Ser Ser Arg Trp Tyr Ile Ser
385             390             395             400

Thr Leu Leu Met Ser Asp Ala Leu Lys Glu Ala Asn Leu Gln Thr Gln
            405             410             415

Val Tyr Asp Ser Leu Leu Trp Tyr Ser Arg Glu Phe Lys Ser Ser Phe
        420             425             430

Asp Met Lys Val Ser Ala Asp Ser Ser Asp Leu Asp Tyr Phe Asn Thr
            435             440             445

Leu Ser Arg Gln His Leu Ala Leu Leu Leu Glu Pro Asp Asp Gln
    450             455             460

Lys Arg Ile Asn Leu Val Asn Thr Phe Ser His Tyr Ile Thr Gly Ala
465             470             475             480

Leu Thr Gln Val Pro Pro Gly Gly Lys Asp Gly Leu Arg Pro Asp Gly
            485             490             495

Thr Ala Trp Arg His Glu Gly Asn Tyr Pro Gly Tyr Ser Phe Pro Ala
            500             505             510

Phe Lys Asn Ala Ser Gln Leu Ile Tyr Leu Leu Arg Asp Thr Pro Phe
    515             520             525

Ser Val Gly Glu Ser Gly Trp Asn Asn Leu Lys Lys Ala Met Val Ser
    530             535             540

Ala Trp Ile Tyr Ser Asn Pro Glu Val Gly Leu Pro Leu Ala Gly Arg
545             550             555             560

His Pro Phe Asn Ser Pro Ser Leu Lys Ser Val Ala Gln Gly Tyr Tyr
            565             570             575

Trp Leu Ala Met Ser Ala Lys Ser Ser Pro Asp Lys Thr Leu Ala Ser
            580             585             590

Ile Tyr Leu Ala Ile Ser Asp Lys Thr Gln Asn Glu Ser Thr Ala Ile
    595             600             605

Phe Gly Glu Thr Ile Thr Pro Ala Ser Leu Pro Gln Gly Phe Tyr Ala
    610             615             620

Phe Asn Gly Gly Ala Phe Gly Ile His Arg Trp Gln Asp Lys Met Val
625             630             635             640

Thr Leu Lys Ala Tyr Asn Thr Asn Val Trp Ser Ser Glu Ile Tyr Asn
            645             650             655

Lys Asp Asn Arg Tyr Gly Arg Tyr Gln Ser His Gly Val Ala Gln Ile
            660             665             670

Val Ser Asn Gly Ser Gln Leu Ser Gln Gly Tyr Gln Gln Glu Gly Trp
    675             680             685

Asp Trp Asn Arg Met Gln Gly Ala Thr Thr Ile His Leu Pro Leu Lys
    690             695             700

Asp Leu Asp Ser Pro Lys Pro His Thr Leu Met Gln Arg Gly Glu Arg
705             710             715             720

Gly Phe Ser Gly Thr Ser Ser Leu Glu Gly Gln Tyr Gly Met Met Ala
            725             730             735

Phe Asp Leu Ile Tyr Pro Ala Asn Leu Glu Arg Phe Asp Pro Asn Phe
            740             745             750

Thr Ala Lys Lys Ser Val Leu Ala Ala Asp Asn His Leu Ile Phe Ile
            755             760             765

Gly Ser Asn Ile Asn Ser Ser Asp Lys Asn Lys Asn Val Glu Thr Thr
    770             775             780

Leu Phe Gln His Ala Ile Thr Pro Thr Leu Asn Thr Leu Trp Ile Asn
```

-continued

```
                785                 790                 795                 800
Gly Gln Lys Ile Glu Asn Met Pro Tyr Gln Thr Thr Leu Gln Gln Gly
                    805                 810                 815

Asp Trp Leu Ile Asp Ser Asn Gly Asn Gly Tyr Leu Ile Thr Gln Ala
                820                 825                 830

Glu Lys Val Asn Val Ser Arg Gln His Gln Val Ser Ala Glu Asn Lys
                835                 840                 845

Asn Arg Gln Pro Thr Glu Gly Asn Phe Ser Ser Ala Trp Ile Asp His
850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
                900                 905                 910

Leu Asp Lys Leu Ser Asn Val Thr Gly Tyr Ala Phe Tyr Gln Pro Ala
                915                 920                 925

Ser Ile Glu Asp Lys Trp Ile Lys Lys Val Asn Lys Pro Ala Ile Val
                930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
                980                 985                 990

Lys Tyr Gln Val Ser Gly Asp Asn Thr Glu Leu Thr Phe Thr Ser Tyr
                995                 1000                1005

Phe Gly Ile Pro Gln Glu Ile Lys Leu Ser Pro Leu Pro
    1010                1015                1020

<210> SEQ ID NO 2
<211> LENGTH: 1021
<212> TYPE: PRT
<213> ORGANISM: Proteus vulgaris

<400> SEQUENCE: 2

Met Pro Ile Phe Arg Phe Thr Ala Leu Ala Met Thr Leu Gly Leu Leu
1               5                   10                  15

Ser Ala Pro Tyr Asn Ala Met Ala Ala Thr Ser Asn Pro Ala Phe Asp
                20                  25                  30

Pro Lys Asn Leu Met Gln Ser Glu Ile Tyr His Phe Ala Gln Asn Asn
            35                  40                  45

Pro Leu Ala Asp Phe Ser Asp Lys Asn Ser Ile Leu Thr Leu Ser
50                  55                  60

Asp Lys Arg Ser Ile Met Gly Asn Gln Ser Leu Leu Trp Lys Trp Lys
65                  70                  75                  80

Gly Gly Ser Ser Phe Thr Leu His Lys Lys Leu Ile Val Pro Thr Asp
                85                  90                  95

Lys Glu Ala Ser Lys Ala Trp Gly Arg Ser Ser Thr Pro Val Phe Ser
            100                 105                 110

Phe Trp Leu Tyr Asn Glu Lys Pro Ile Asp Gly Tyr Leu Thr Ile Asp
        115                 120                 125

Phe Gly Glu Lys Leu Ile Ser Thr Ser Glu Ala Gln Ala Gly Phe Lys
    130                 135                 140
```

-continued

```
Val Lys Leu Asp Phe Thr Gly Trp Arg Ala Val Gly Val Ser Leu Asn
145                 150                 155                 160

Asn Asp Leu Glu Asn Arg Glu Met Thr Leu Asn Ala Thr Asn Thr Ser
            165                 170                 175

Ser Asp Gly Thr Gln Asp Ser Ile Gly Arg Ser Leu Gly Ala Lys Val
        180                 185                 190

Asp Ser Ile Arg Phe Lys Ala Pro Ser Asn Val Ser Gln Gly Glu Ile
    195                 200                 205

Tyr Ile Asp Arg Ile Met Phe Ser Val Asp Asp Ala Arg Tyr Gln Trp
210                 215                 220

Ser Asp Tyr Gln Val Lys Thr Arg Leu Ser Glu Pro Glu Ile Gln Phe
225                 230                 235                 240

His Asn Val Lys Pro Gln Leu Pro Val Thr Pro Glu Asn Leu Ala Ala
                245                 250                 255

Ile Asp Leu Ile Arg Gln Arg Leu Ile Asn Glu Phe Val Gly Gly Glu
            260                 265                 270

Lys Glu Thr Asn Leu Ala Leu Glu Glu Asn Ile Ser Lys Leu Lys Ser
        275                 280                 285

Asp Phe Asp Ala Leu Asn Ile His Thr Leu Ala Asn Gly Gly Thr Gln
    290                 295                 300

Gly Arg His Leu Ile Thr Asp Lys Gln Ile Ile Ile Tyr Gln Pro Glu
305                 310                 315                 320

Asn Leu Asn Ser Gln Asp Lys Gln Leu Phe Asp Asn Tyr Val Ile Leu
                325                 330                 335

Gly Asn Tyr Thr Thr Leu Met Phe Asn Ile Ser Arg Ala Tyr Val Leu
            340                 345                 350

Glu Lys Asp Pro Thr Gln Lys Ala Gln Leu Lys Gln Met Tyr Leu Leu
        355                 360                 365

Met Thr Lys His Leu Leu Asp Gln Gly Phe Val Lys Gly Ser Ala Leu
    370                 375                 380

Val Thr Thr His His Trp Gly Tyr Ser Ser Arg Trp Trp Tyr Ile Ser
385                 390                 395                 400

Thr Leu Leu Met Ser Asp Ala Leu Lys Glu Ala Asn Leu Gln Thr Gln
                405                 410                 415

Val Tyr Asp Ser Leu Leu Trp Tyr Ser Arg Glu Phe Lys Ser Ser Phe
            420                 425                 430

Asp Met Lys Val Ser Ala Asp Ser Ser Leu Asp Tyr Phe Asn Thr
    435                 440                 445

Leu Ser Arg Gln His Leu Ala Leu Leu Leu Glu Pro Asp Asp Gln
450                 455                 460

Lys Arg Ile Asn Leu Val Asn Thr Phe Ser His Tyr Ile Thr Gly Ala
465                 470                 475                 480

Leu Thr Gln Val Pro Pro Gly Gly Lys Asp Gly Leu Arg Pro Asp Gly
                485                 490                 495

Thr Ala Trp Arg His Glu Gly Asn Tyr Pro Gly Tyr Ser Phe Pro Ala
            500                 505                 510

Phe Lys Asn Ala Ser Gln Leu Ile Tyr Leu Leu Arg Asp Thr Pro Phe
        515                 520                 525

Ser Val Gly Glu Ser Gly Trp Asn Asn Leu Lys Lys Ala Met Val Ser
    530                 535                 540

Ala Trp Ile Tyr Ser Asn Pro Glu Val Gly Leu Pro Leu Ala Gly Arg
545                 550                 555                 560

His Pro Phe Asn Ser Pro Ser Leu Lys Ser Val Ala Gln Gly Tyr Tyr
```

```
                565                 570                 575
Trp Leu Ala Met Ser Ala Lys Ser Ser Pro Asp Lys Thr Leu Ala Ser
            580                 585                 590

Ile Tyr Leu Ala Ile Ser Asp Lys Thr Gln Asn Glu Ser Thr Ala Ile
            595                 600                 605

Phe Gly Glu Thr Ile Thr Pro Ala Ser Leu Pro Gln Gly Phe Tyr Ala
            610                 615                 620

Phe Asn Gly Gly Ala Phe Gly Ile His Arg Trp Gln Asp Lys Met Val
625                 630                 635                 640

Thr Leu Lys Ala Tyr Asn Thr Asn Val Trp Ser Ser Glu Ile Tyr Asn
                645                 650                 655

Lys Asp Asn Arg Tyr Gly Arg Tyr Gln Ser His Gly Val Ala Gln Ile
                660                 665                 670

Val Ser Asn Gly Ser Gln Leu Ser Gln Gly Tyr Gln Gln Glu Gly Trp
            675                 680                 685

Asp Trp Asn Arg Met Glu Gly Ala Thr Thr Ile His Leu Pro Leu Lys
            690                 695                 700

Asp Leu Asp Ser Pro Lys Pro His Thr Leu Met Gln Arg Gly Glu Arg
705                 710                 715                 720

Gly Phe Ser Gly Thr Ser Ser Leu Glu Gly Gln Tyr Gly Met Met Ala
                725                 730                 735

Phe Asn Leu Ile Tyr Pro Ala Asn Leu Glu Arg Phe Asp Pro Asn Phe
            740                 745                 750

Thr Ala Lys Lys Ser Val Leu Ala Ala Asp Asn His Leu Ile Phe Ile
            755                 760                 765

Gly Ser Asn Ile Asn Ser Ser Asp Lys Asn Lys Asn Val Glu Thr Thr
770                 775                 780

Leu Phe Gln His Ala Ile Thr Pro Thr Leu Asn Thr Leu Trp Ile Asn
785                 790                 795                 800

Gly Gln Lys Ile Glu Asn Met Pro Tyr Gln Thr Thr Leu Gln Gln Gly
                805                 810                 815

Asp Trp Leu Ile Asp Ser Asn Gly Asn Gly Tyr Leu Ile Thr Gln Ala
            820                 825                 830

Glu Lys Val Asn Val Ser Arg Gln His Gln Val Ser Ala Glu Asn Lys
            835                 840                 845

Asn Arg Gln Pro Thr Glu Gly Asn Phe Ser Ser Ala Trp Ile Asp His
            850                 855                 860

Ser Thr Arg Pro Lys Asp Ala Ser Tyr Glu Tyr Met Val Phe Leu Asp
865                 870                 875                 880

Ala Thr Pro Glu Lys Met Gly Glu Met Ala Gln Lys Phe Arg Glu Asn
                885                 890                 895

Asn Gly Leu Tyr Gln Val Leu Arg Lys Asp Lys Asp Val His Ile Ile
            900                 905                 910

Leu Asp Lys Leu Ser Asn Val Thr Gly Tyr Ala Phe Tyr Gln Pro Ala
            915                 920                 925

Ser Ile Glu Asp Lys Trp Ile Lys Lys Val Asn Lys Pro Ala Ile Val
            930                 935                 940

Met Thr His Arg Gln Lys Asp Thr Leu Ile Val Ser Ala Val Thr Pro
945                 950                 955                 960

Asp Leu Asn Met Thr Arg Gln Lys Ala Ala Thr Pro Val Thr Ile Asn
                965                 970                 975

Val Thr Ile Asn Gly Lys Trp Gln Ser Ala Asp Lys Asn Ser Glu Val
            980                 985                 990
```

```
Lys Tyr Gln Val Ser Gly Asp Asn  Thr Glu Leu Thr Phe  Thr Ser Tyr
        995             1000              1005

Phe Gly  Ile Pro Gln Glu Ile  Lys Leu Ser Pro Leu  Pro
    1010             1015             1020
```

AGENT FOR NEUROPATHIC PAIN

This application is a Divisional Application of prior application Ser. No. 12/937,456, filed on Mar. 1, 2011, which is a 371 National Stage application of PCT/JP2009/057503, filed on Apr. 14, 2009, which is hereby incorporated by reference.

TECHNICAL FIELD

The present invention relates to an improving agent for neuropathic pain useful as a therapeutic agent for allodynia or the like.

BACKGROUND ART

Neuropathic pain is a type of pain caused by damage to the central nervous or the peripheral nervous and includes symptoms such as a hyperalgesic response in which the threshold to spontaneous pain or invasive stimulation is decreased, and mechanical allodynia in which non-invasive mechanical stimulation or tactile stimulation which does not usually cause pain is mistakenly perceived as severe pain. Neuropathic pain, particularly allodynia is characterized in that intractable burning pain or stabbing pain lasts continuously for a long time and causes a decrease in the effectiveness of rehabilitation due to pain or the like, and is a pathological condition that significantly decreases the QOL of patients. It can be said that there is almost no satisfactory drug therapy for neuropathic pain and the development of a drug that satisfies both efficacy and safety for neuropathic pain has been demanded. However, the development of such a drug has not progressed as it should have. One of the reasons for this is considered to be that the mechanism of pathogenesis is not single and several mechanisms are intricately involved in the onset of the disease. The detailed pathogenic mechanisms of allodynia have not been elucidated yet, however, involvement of abnormal neuronal circuit formation due to an organic change and a functional change in neurons in the pain transmission pathway including nociceptive neurons has been proposed recently. Here, as the organic change, a phenomenon in which $A\beta$ fibers terminating in laminae III-V of the spinal cord dorsal horn elongate its sprout axon into lamina II of the spinal cord dorsal horn which is the center of the pain transmission called substantia gelatinosa after a nerve injury can be exemplified. As the functional change, a phenomenon in which $A\beta$ fibers presynaptically activate C fibers via interneurons, and the like can be exemplified (Non-patent document 1). Further, as a new factor for inducing abnormal neuronal circuit formation, involvement of expression of a guidance molecule which guides nerve fibers to a specific site and of release of a neuronal activator such as BDGF (brain-derived growth factor) or the like which is an allodynia enhancing factor accompanying the activation of spinal microglia has been proposed (Non-patent document 2).

As pathological conditions exhibiting neuropathic pain, diseases caused by central nervous disorders and peripheral nervous disorders are known. Examples of the central nervous disease include brain disorders, multiple sclerosis, and spinal cord injuries, and examples of the peripheral nervous disease include diabetes and herpes zoster.

In the current treatment of neuropathic pain, nonsteroidal antiinflammatory drugs (NSAIDs), opioid analgesics, and analgesic adjuvants (such as an NMDA receptor antagonist, an antidepressant, an antiarrhythmic, an anticonvulsant, or an antispasmodic) are used, however, neuropathic pain is resistant to therapy using NSAIDs and opioid analgesics, and it is very difficult to control with medication. Further, other than NSAIDs and opioid analgesics, as the analgesic adjuvant, an antidepressant (such as a tricyclic type, a tetracyclic type, an SSRI (a selective serotonin reuptake inhibitor), or an SNRI (a selective serotonin-noradrenaline reuptake inhibitor)), an anticonvulsant (such as carbamazepine), an antispasmodic (baclofen), an antiarrhythmic (such as lidocaine), an NMDA receptor antagonist (such as ketamine), a steroid (such as betamethasone), a therapeutic agent for pain based on the activation of a descending pain inhibitory system (Neurotropin, a formulation containing an extract isolated from the inflamed skin of rabbits inoculated with a vaccinia virus which is approved as a therapeutic agent for postherpetic neuralgia and the like), or the like is used (Non-patent document 3). However, the current situation is that these medicinal agents for improving peripheral pain have strong adverse reactions, and the medicinal agents for central pain have a low efficacy, and therefore, the development of a medicinal agent having a more stable and higher therapeutic effectiveness has been demanded.

On the other hand, in the central nervous system, a proteoglycan is considered to exert an activity of regulating various neuronal functions such as an axon guidance function by binding to various growth factors, cell adhesion factors, and so on (Non-patent documents 4 and 5). In central nervous diseases such as a spinal cord injury, it is known that a proteoglycan having chondroitin sulfate side chain is a neuronal axonal regeneration inhibitory factor which forms a glial scar in an injured area thereof. It has been reported that chondroitinase ABC, which is an enzyme capable of degrading chondroitin sulfate, dermatan sulfate (also referred to as chondroitin sulfate B), and the like forming a side chain of a proteoglycan, degrades a chondroitin sulfate side chain (including a dermatan sulfate side chain, hereinafter, the same shall apply) of a proteoglycan expressed in a glial scar in a spinal cord injury rat model and has an activity of improving a hind limb motor function (Non-patent document 8). It is considered that the neuronal axonal regeneration inhibitory activity of a chondroitin sulfate proteoglycan is exhibited mainly through an activation of Rho kinase (Non-patent document 6). On the other hand, it has been reported that ATP known as a pain substance strongly activates spinal microglia and causes an increase in the production of various mediators which promote abnormal neuronal circuit formation, synaptic trafficking accompanied by cytoskeletal reconstruction, or a release of a neurotransmitter and is involved in neuropathic pain. ATP activates also Rac which is a member of the Rho family (Non-patent document 7).

Further, it has been revealed that spinal microglia of the spinal cord dorsal horn are activated by a nerve injury, and stimulation of P2X4 receptors strongly expressed there causes neuropathic pain, and it has been proposed that the Rho kinase signal transduction pathway is involved as one of the pathways of these activation cascades (Non-patent document 7).

The efficacy of a chondroitinase in the treatment of a motor function for an injury of the central nervous system has been supported not only by, for example, Non-patent document 8, but also by Patent document 1 and the like. However, the efficacy as described in these documents means or intends that a function (such as a motor function) or a sensation which is lost by a nervous disorder is restored or recovered by degrading a chondroitin sulfate side chain of a proteoglycan and promoting the regeneration of injured neuronal axons or the like, and there is no reported case of an improving activity of a chondroitinase for pain caused by a nervous disorder as far as the present inventors have known. It is considered that it cannot be said that there is not at all an association between a recovery effect on a motor function or the like and an effect on neuropathic pain, however, at least there is no technical common knowledge that if there is a recovery effect on a motor function or the like, an improving effect on neuropathic pain is exhibited or can be expected. In fact, Bradbury, E. J. et al. confirmed a recovery efficacy of a chondroitinase on a motor function in a spinal cord injury rat model, however, they have reported that a recovery efficacy on a sensory function was not obtained (Non-patent document 8). Further, in the study of abnormal pain of human patients with a spinal cord injury (Non-patent document 9), an association between the level of residual motor ability and the presence or absence of abnormal pain such as allodynia is not observed, and therefore, the recovery of a motor function is not associated with the recovery of neuropathic pain.

On the other hand, it is known that abnormal elongation of primary afferent nerves adversely affect the function of nociceptive neurons and can lead to abnormal hypersensitivity to pain stimulations. Barritt, A. W. et al. studied the possibility in which the plasticity induced by a treatment with chondroitinase ABC after a spinal cord injury (a lumbar spinal injury) has adverse reactions. As a result of the study, they confirmed that the elongation of primary afferent nerves was observed, but connectivity of nociceptive neurons or development of mechanical allodynia or thermal hyperalgesia was not observed by the treatment (Non-patent document 10).

Accordingly, it has not been known so far that a chondroitinase has an activity of improving neuropathic pain.

Patent document 1: JP-T-2005-526740 (WO 2003/074080)

Non-patent document 1: MINAMI Toshiaki, et al., "Plasticity of pain", Seibutsu Butsuri, 41(1), 15-19 (2001)

Non-patent document 2: TSUDA Makoto, "A new mechanism of neuropathic pain through ATP receptors in spinal microglia", Folia Pharmacologica Japonica, 129, 349-353 (2007)

Non-patent document 3: ISEKI Masako et al., "Current clinical status of and future expectations for pain alleviation agents", Folia Pharmacologica Japonica, 128, 326-329 (2006)

Non-patent document 4: Crespo, D. et al., 2007, How does chondroitinase promote functional recovery in the damaged CNS?, Experimental Neurology 206 (2), 159-71

Non-patent document 5: Wit, J. D. et al., 2007, Semaphorins: Receptor and Intracellular Signaling Mechanisms, Chapter 7, Proteoglycans as Modulators of Axon Guidance Cue Function, 73-89

Non-patent document 6: Monnier, P. P. et al., 2003, The Rho/ROCK pathway mediates neurite growth-inhibitory activity associated with the chondroitin sulfate proteoglycans of the CNS glial scar, Mol. Cell. Neurosci. 22, 319-330

Non-patent document 7: Honda, S. et al., 2001, Extracellular ATP or ADP Induce Chemotaxis of Cultured Microglia through Gi/o-Coupled P2Y Receptors, J. Neurosci. 21(6), 1975-1982

Non-patent document 8: Bradbury, E. J. et al., 2002, Chondroitinase ABC promotes functional recovery after spinal cord injury, Nature 416, 636-640

Non-patent document 9: Specified Non-profit Corporation, JAPAN SPINAL CORD FOUNDATION (JSCF), Fact-finding report publication about abnormal sharp pain with the SCI), September, 2004, Non-patent document 10: Barritt, A. W. et al., 2006, Chondroitinase ABC promotes sprouting of intact and injured spinal systems after spinal cord injury, Journal of Neuroscience 26(42), 10856-10867

DISCLOSURE OF THE INVENTION

Problems that the Invention is to Solve

An object of the present invention is to provide a substance which can be used as an active ingredient of an improving agent for neuropathic pain having a novel mechanism of action different from those of currently available agents and, therefore, provide an improving agent for neuropathic pain which rarely interacts with currently available agents and also does not have adverse reactions similar to those of currently available agents.

Means for Solving the Problems

The present inventors found that activation of Rho kinase is a common intracellular transduction pathway involved in neuronal axonal regeneration inhibition and pathological formation such as development of neuropathic pain, and made a hypothesis, by considering the above-mentioned biological activity of a proteoglycan, that a proteoglycan having chondroitin sulfate side chain induces continuous abnormal activation of neurons, glial cells, or the like after a nervous disorder such as a nerve injury, and also guides sensory nerves to the pain transmission pathway so as to induce abnormal neuronal circuit formation, such that it is involved in the development of neuropathic pain, particularly allodynia.

Then, the present inventors conceived that if an enzyme having an activity of degrading a chondroitin sulfate chain of a chondroitin sulfate proteoglycan (hereinafter, also referred to as CSPG) such as a chondroitinase is continuously administered to the injured site of an individual starting from immediately after the occurrence of a nervous disorder, for example, a spinal cord injury to remove the chondroitin sulfate chain of the chondroitin sulfate proteoglycan, the continuous abnormal activation of neurons or non-neuronal cells such as glial cells caused by the proteoglycan is canceled, and this canceling leads to the cancellation of the neuronal axon guidance function of the proteoglycan and consequently achieving a therapeutic effectiveness on neuropathic pain. Based on the conception, the present inventors continuously administered a lyase (an elimination enzyme, hereinafter, the same shall apply) such as a chondroitinase having an activity of degrading a chondroitin sulfate chain of a chondroitin sulfate proteoglycan to an injured site in the intrathecal space of a spinal cord injury rat model, thereby promoting the improvement of a sensory nerve function, and therefore, they found for the first time that the enzyme can improve neuropathic pain due to a hyperalgesic response, particularly allodynia.

An improving agent for neuropathic pain due to a hyperalgesic response according to the present invention (hereinafter, also referred to as the improving agent of the present invention) made on the basis of the above finding is characterized by comprising, as an active ingredient, a lyase having an activity of degrading a chondroitin sulfate chain of a chondroitin sulfate proteoglycan as described in claim 1.

Further, the improving agent according to claim 2 is characterized in that, in the improving agent according to claim 1, the lyase is chondroitinase ABC.

Further, the improving agent according to claim 3 is characterized in that, in the improving agent according to claim 1 or 2, the neuropathic pain due to a hyperalgesic response is allodynia.

Further, the improving agent according to claim 4 is characterized in that, in the improving agent according to any one of claims 1 to 3, the neuropathic pain due to a hyperalgesic response is neuropathic pain caused by a central nervous disorder.

Further, the improving agent according to claim 5 is characterized in that, in the improving agent according to claim 4, the central nervous disorder is a spinal cord injury.

Effect of the Invention

The present invention is based on the fact that the present inventors found that chondroitinase ABC which is one of the lyases degrading chondroitin sulfate forming a side chain of a proteoglycan into unsaturated disaccharides improves neuropathic pain caused by a nervous disorder.

More specifically, based on an overall consideration made by the present inventors with respect to various findings having been reported so far as described above, a possibility that a proteoglycan having a chondroitin sulfate side chain functions as an aggravating factor for abnormal neuronal circuit formation in the spinal cord dorsal horn after a nerve injury and a possibility that an inhibitory effect on abnormal neuronal circuit formation is obtained by degrading and removing the chondroitin sulfate chain of the proteoglycan were assumed, and as a method for removing the proteoglycan, chondroitinase ABC which can degrade chondroitin sulfate was selected and the selected substance was continuously administered intrathecally. As a result, it was found that the substance has an improving activity on a sensory nerve function and also has an improving effect on neuropathic pain due to a hyperalgesic response, particularly allodynia. This finding was found for the first time by the present inventors this time, and based on this finding, the present invention provides a novel improving agent for neuropathic pain through the inhibition of abnormal neuronal circuit formation as a basic concept by a lyase having an activity of degrading a chondroitin sulfate side chain of a proteoglycan.

According to the present invention, an improving agent for neuropathic pain due to a hyperalgesic response and a therapeutic agent for allodynia, each containing, as an active ingredient, a lyase such as a chondroitinase having an activity of degrading a chondroitin sulfate chain of a chondroitin sulfate proteoglycan, for example, chondroitinase ABC which is a lyase degrading chondroitin sulfate forming a side chain of a proteoglycan into unsaturated disaccharides are provided. The improving agent for neuropathic pain of the present invention has a novel mechanism of action different from those of opioid analgesics and analgesic adjuvants currently used for the treatment of pain. Therefore, according to the present invention, an unprecedented novel method for treating pain which rarely interacts with currently available agents and also does not have adverse reactions similar to those of currently available agents can be provided.

Further, according to the present invention, a method for preventing or improving abnormal neuronal circuit formation after a nervous disorder by enzymatically degrading a chondroitin sulfate proteoglycan which abnormally increases in the injured site or impairing the function thereof can be provided.

Further, according to the present invention, a method for improving neuropathic pain including allodynia can be provided by, in an injured site, for example, inhibiting activation of Rho kinase, degrading a chondroitin sulfate side chain or a dermatan sulfate side chain of a proteoglycan which guides the pathway of elongation of neuronal axons, or impairing the function of a proteoglycan.

Further, according to the present invention, a method for restoring or recovering a function (such as a motor function) or the like which is lost by a nervous disorder as well as improving neuropathic pain due to a hyperalgesic response including allodynia by continuously administering a low dosage of a lyase having an activity of degrading a chondroitin sulfate chain of a chondroitin sulfate proteoglycan, particularly a chondroitin sulfate degrading enzyme such as chondroitinase ABC to the injured site (for example, in the subarachnoid cavity (in the intrathecal space)) for a given period of time after the occurrence of the nervous disorder can be provided.

Specifically, according to the present invention, an agent for the application to a nervous disorder for continuously administering a lyase having an activity of degrading a chondroitin sulfate chain of a chondroitin sulfate proteoglycan at a dose of 6 mU to 15000 mU per human adult per day to an injured site of the nervous disorder, characterized by containing the enzyme as an active ingredient, and a method for continuously administering the agent for a period from immediately after to 3 days after receiving an injury up to 8 weeks can be provided.

BEST MODE FOR CARRYING OUT THE INVENTION

The improving agent of the present invention is characterized by comprising, as an active ingredient, a lyase having an activity of degrading a chondroitin sulfate chain of a chondroitin sulfate proteoglycan.

The enzyme which can be used as the active ingredient of the improving agent of the present invention (hereinafter, also referred to as the enzyme of the present invention) is not particularly limited as long as it is a lyase having an activity of degrading a chondroitin sulfate chain of a chondroitin sulfate proteoglycan which can be present in the nervous system (such as Neurocan, Phosphacan, RPTP, Brevican, NG2, Versican, Aggrican, Decorin, Biglycan, or CD44) by an elimination reaction, however, generally, a lyase called a chondroitinase (a chondroitin sulfate degrading enzyme) is preferred.

The chondroitinase is a lyase which degrades chondroitin sulfate into unsaturated disaccharides in an eliminating manner, and a chondroitinase derived mainly from a microorganism is preferred as the enzyme to be used as the active ingredient of the improving agent of the present invention. As the chondroitinase, the following chondroitinase ABC is particularly preferred.

Chondroitinase ABC (EC 4.2.2.20 or EC 4.2.2.4) is an enzyme that mainly produces unsaturated disaccharides having a Δ4-hexuronic acid residue at the nonreducing terminal by cleaving an N-acetylhexosaminide linkage in a glycosaminoglycan including chondroitin sulfate through an elimination reaction, and is an enzyme that strongly catalyzes the degradation of chondroitin sulfate A derived from mammalian cartilage (having a high chondroitin-4-sulfate content), chondroitin sulfate C derived from shark cartilage (having a high chondroitin-6-sulfate content), and chondroitin sulfate B derived from mammalian skin (dermatan sulfate), and weakly catalyzes the degradation of hyaluronic acid, and degrades also chondroitin sulfate A, dermatan sulfate, and chondroitin sulfate C in a chondroitin sulfate side chain of a chondroitin sulfate proteoglycan (Yamagata, T. et al., J. Biol. Chem., 243: 1523-1535 (1968), Hamai A. et al., J. Biol. Chem. 272: 9123-9130 (1997)). As a reagent for research for removing a mucopolysaccharide from an animal tissue or for identifying a mucopolysaccharide in a tissue, this enzyme is commercially available as a reagent from Seikagaku Biobusiness Corporation and the commercial products of the enzyme produced by bacteria such as *Proteus vulgaris* have a code No. 100330 (Chondroitinase ABC (*Proteus vulgaris*)) and a code No. 100332 (Chondroitinase ABC Protease Free (*Proteus vulgaris*)). Other than these, an enzyme purified to a high purity (which is a single protein and does not contain endotoxins, nucleic acids, contaminant proteins, etc.) and having an extremely high specific activity is more preferred because a clinical trial using it has been performed as a therapeutic agent for intervertebral disc herniation and the activity thereof on the living body has been sufficiently elucidated. In particular, chondroitinase ABC having a high purity and a high specific activity described in Japanese Patent No. 3980657, U.S. Pat. Nos. 6,184,023, 5,773,277, and 5,763,205 is most preferred. Incidentally, the above-mentioned chondroitinase ABC is the same enzyme as the following enzymes with other names.

Chondroitinase ABC Type 1
Chondroitin ABC endolyase 1
Chondroitin ABC lyase I
Chondroitin sulfate endolyase
Chondroitin ABC eliminase Further, a gene of a substance having the above-mentioned chondroitinase ABC activity has been cloned, and the amino acid sequence of the protein thereof and also the nucleotide sequence of the DNA encoding the protein have been identified (U.S. Pat. No. 5,578,480, JP-T-2007-520447 (WO2004/103299)). As a typical amino acid sequence, an amino acid sequence represented by Sequence Listing No. 1 described in U.S. Pat. No. 5,578,480 can be exemplified. This amino acid sequence comprises 1021 amino acid residues, wherein amino acids 1 to 24 form a signal sequence and a mature protein comprises 997 amino acid residues (amino acids 25 to 1021). Further, as another typical amino acid sequence, an amino acid sequence represented by Sequence Listing No. 2 described in the amino acid sequence database (UniProtKB/Swiss-Prot: Entry name CABC_PROVU, Primary accession number P59807, Protein name Chondroitin ABC endolyase 1 [Precursor]) can be exemplified. This amino acid sequence also comprises 1021 amino acid residues, however, it is different from the amino acid sequence represented by Sequence Listing No. 1 in two amino acids (amino acid 694: Q→E, amino acid 738: D→N). Further, the amino acid sequence described in SEQ ID NO: 1 of U.S. Patent Application Publication No. 2006/0233782 is that of a mature protein, and therefore comprises 997 amino acid residues, however, it is different from the amino acid sequence ranging from amino acids 25 to 1021 of the amino acid sequence represented by Sequence Listing No. 1 in four amino acids (amino acid 154: A→T, amino acid 295: I→T, amino acid 694: Q→E, amino acid 738: D→N). That is, even an enzyme having an amino acid sequence with a substitution of at least four amino acids (for example, amino acids 154, 295, 694, and 738) on the basis of the amino acid sequence represented by Sequence Listing No. 1 can be regarded as an enzyme having a comparable chondroitinase ABC activity.

(Other Reference Information)
KEGG Genes
ype: YP00824
hypothetical protein [EC:4.2.2.20 4.2.2.21]; K08961 chondroitin-sulfate-ABC endolyase; K08962 chondroitin-sulfate-ABC exolyase; [Sanger:YP00824] [NCBI-GI: 16121135] [NCBI-Gene ID: 1173663] [UniProt: Q0WIL0] ypk: y3211 ypk: y3211
chondroitin lyase [EC:4.2.2.20 4.2.2.21]; K08961 chondroitin-sulfate-ABC endolyase; K08962 chondroitin-sulfate-ABC exolyase; [NCBI-GI: 22127087] [NCBI-Gene ID: 1148158] [UniProt: Q8CZX2] ypa: YPA_0445 ypa: YPA_0445
hypothetical protein [EC:4.2.2.20 4.2.2.21]; K08961 chondroitin-sulfate-ABC endolyase; K08962 chondroitin-sulfate-ABC exolyase; [JGI: YPA0445] [NCBI-GI: 108806442] [NCBI-Gene ID: 4121007] [UniProt: Q1CAV9] ypn: YPN_3027
ypn: YPN_3027
chondroitin-sulfate-ABC endolyase/chondroitin-sulfate-ABC exolyase [EC:4.2.2.20 4.2.2.21]; K08961 chondroitin-sulfate-ABC endolyase; K08962 chondroitin-sulfate-ABC exolyase; [NCBI-GI:108813187] [NCBI-Gene ID: 4125950] [UniProt: Q1CF76] yps: YPTB3073 yps:YPTB3073
possible chondroitin ABC lyase [EC:4.2.2.20 4.2.2.21]; K08961 chondroitin-sulfate-ABC endolyase; K08962 chondroitin-sulfate-ABC exolyase; [NBI-GI: 51597387] [NCBI-Gene ID: 2954593] [UniProt: Q667C0]Entrez Gene GENE ID 2827933

Further, a plurality of mutated proteins of chondroitinase ABC (including fragmented proteins having the enzymatic activity) have also been produced, and these enzymes produced by genetic recombination are also included in the present invention as long as they can function as an active ingredient of the improving agent of the present invention (see, for example, JP-T-2007-516229 (WO 2004/110359), JP-T-2007-532094 (WO 2004/110360), JP-T-2007-520447 (WO 2004/103299), WO 2005/087920, etc.).

Further, chondroitinase ABC (Type 2) which is different from the above-mentioned chondroitinase ABC (Type 1) has also been isolated and purified from *Proteus vulgaris* and then subjected to cloning, and these enzymes are also included in the present invention as long as they can function as an active ingredient of the improving agent of the present invention (see, Hamai A. et al., J. Biol. Chem. 272: 9123-9130 (1997), U.S. Pat. Nos. 5,741,692 and 5,498,536, etc.).

Incidentally, chondroitinase ABC which is purified to a high purity and has an extremely high specific activity described in Japanese Patent No. 3980657, U.S. Pat. Nos. 6,184,023, 5,773,277, and 5,763,205 is an enzyme which does not include the above-mentioned Type 2, and is most preferred as an active ingredient of the improving agent of the present invention. That is, the improving agent of the present invention is a pharmaceutical product aiming at the administration to a human body or the like, and therefore, it is preferred that chondroitinase ABC which is used as the active ingredient has a pharmaceutically acceptable grade and impurities derived from a microorganism that produces this enzyme such as endotoxins, nucleic acids, and proteases are removed as much as possible. It is preferred that the amounts of endotoxins, nucleic acids, and proteases are not higher than the detection limits by a common analytical method, and for example, the amount of endotoxins is preferably 5.0 pg/100 U or less when measurement is performed using Toxicolor (registered trademark) system manufactured by Seikagaku Corporation. Further, the amount of nucleic acids is preferably not higher than the detection limit when measurement is performed by a threshold method (DNA analyzer: Threshold (manufactured by Molecular Device Corporation)). The amount of proteases is preferably 0.1% or less of the total protein when measurement is performed using FITC-casein as a substrate.

The origin of chondroitinase ABC is not limited to the above-mentioned *Proteus vulgaris*, and chondroitinase ABC may be derived from other bacterium belonging to the genus *Proteus*, and moreover, it may be derived from a bacterium belonging to the genus *Bacteroides* such as *Bacteroides stercoris* (see Hong S W. et al., Eur J Biochem. 2002 June; 269(12): 2934-40).

The enzyme which is the active ingredient of the improving agent of the present invention, that is, a lyase having an activity of degrading CSPG can effectively degrade and remove a chondroitin sulfate side chain and a dermatan sulfate side chain of a proteoglycan expressed in an injured site of a spinal cord injury or can impair the function thereof by directly administering the lyase to the injured site. As a target molecule, Neurocan, Phosphacan, RPTP, Brevican, NG2, Versican, Aggrican, Decorin, Biglycan, CD44, and the like, which are each a proteoglycan having a chondroitin sulfate and/or dermatan sulfate side chain expressed in astrocytes, oligodendrocytes, microglia, neurons, and the like, which constitute central nerve tissues, can be exemplified. As is presumed from the fact that there are a lot of molecular species, the activity of such a proteoglycan having a chondroitin sulfate side chain and/or a dermatan sulfate side chain on neurophysiological functions including a central nerve regeneration phenomenon is very versatile, and much of which is still unknown. However, from the past studies, it has been proposed that there are two main activities: one activity is exhibited as a neuronal axonal regeneration inhibitory molecule; and the other activity is exhibited as a neuronal axon guidance molecule. The former is the activity of inhibiting nerve regeneration, and the latter is the activity of promoting nerve regeneration. The present inventors found that there is a possibility that CSPG may induce and promote abnormal neuronal circuit formation. Since the abnormal neuronal circuit formation after a nerve injury leads to the occurrence of neuropathic pain such as allodynia occurring after a spinal cord injury, it was found that by degrading CSPG which abnormally increases in an injured site after a nervous disorder with the enzyme of the present invention which is the active ingredient of the improving agent of the present invention, that is, a lyase having an activity of degrading CSPG, it is possible to prevent or treat the occurrence of neuropathic pain.

The active ingredient of the improving agent of the present invention is formulated into a parenteral preparation by a common procedure in the same manner as a conventional parenteral enzyme preparation, is parenterally (intravenously, subcutaneously, intrathecally (into the intrathecal space), intradermally, intramuscularly, internodally, percutaneously, or the like) administered to a mammal (such as human, non-human primate, rat, mouse, rabbit, cattle, horse, pig, dog, or cat) through an administration route appropriate to a target disease, and is used for treating or preventing the target disease of the animal.

Examples of the parenteral preparation include liquid preparations (such as solution preparations, suspensions, and ophthalmic preparations), solid preparations (such as lyophilized preparations, powder preparations, granule preparations, microcapsules, liposomes, and lipospheres), and semi-solid preparations (such as ointments). For example, in the case where the medicinal agent of the present invention is produced as a liquid preparation, the liquid preparation can be produced by dissolving or dispersing the enzyme of the present invention of a pharmaceutically acceptable grade in water for injection or a solution obtained by appropriately adding the water, a pharmaceutically acceptable additive or carrier such as a isotonic agent (such as sodium chloride, potassium chloride, glycerin, mannitol, sorbitol, boric acid, borax, glucose, or propylene glycol), a buffer agent (such as a phosphoric acid buffer, an acetic acid buffer, a boric acid buffer, a carbonic acid buffer, a citric acid buffer, a Tris buffer, a glutamic acid buffer, or an ε-aminocaproic acid buffer), a preservative (such as a p-hydroxybenzoic acid ester, chlorobutanol, benzyl alcohol, benzalkonium chloride, sodium dehydroacetate, sodium edetate, boric acid, or borax), a nonionic surfactant (such as a polyoxyethylene sorbitan fatty acid ester, polyoxyethylene hydrogenated castor oil, a sucrose fatty acid ester, or polyoxyethylene polyoxypropylene glycol), a thickener (such as polyvinyl alcohol), a stabilizing and activity retaining agent (such as serum albumin, gelatin, sucrose (saccharose), polyethylene glycol, a dextran, lactose, maltose, mannitol, xylitol, sorbitol, inositol, sodium edetate, sodium citrate, or ascorbic acid), a pH adjusting agent (such as hydrochloric acid, sodium hydroxide, phosphoric acid, or acetic acid), a solubilizing agent, an antioxidant, a substance effective for preventing adsorption onto a container, or the like. Further, the medicinal agent of the present invention can be formulated into a solid preparation for dissolution before use by drying such a liquid preparation through a drying method (such as lyophilization) which does not affect the pharmacological function such as an activity of the enzyme of the present invention. As a specific example, a liquid preparation can be prepared by dissolving or suspending the enzyme of the present invention of a pharmaceutically acceptable grade in physiological saline, water for injection, an isotonic solution, an oily solution, or the like.

Further, the medicinal agent of the present invention can also be formulated into a sustained-release preparation using a hydrogel such as Duraseal (trademark) I (available from Confluent Surgical, Inc.), Duraseal (trademark) II (available from Confluent Surgical, Inc.), or Spray Gel. Duraseal (trademark, collagen based on a gel foam).

The medicinal agent as prepared as described above is administered through an administration method appropriate to the target disease, severity of the symptoms, subject in need of administration, and the like, and improvement (cure or prevention of occurrence) of neuropathic pain can be achieved. For example, as one example of the administration method, a method of topically administering the medicinal agent to an injured site of a nervous disorder or a periphery thereof can be exemplified. More specifically, a method of continuously administering the medicinal agent, for example, in the subarachnoid cavity (in the intrathecal space) by an osmotic pump using a microtube can be exemplified.

The dosage and duration of administration of the medicinal agent prepared using the improving agent of the present invention should be appropriately determined by a health care professional such as a medical doctor according to the conditions including the target disease, animal species in need of administration, age and body weight, severity of the symptoms, and health conditions, and are not particularly limited. That is, the dosage and duration of administration of the medicinal agent may be effective dosage and duration for, for example, inhibiting activation of Rho kinase, or degrading a chondroitin sulfate side chain and a dermatan sulfate side chain of a proteoglycan which guides the pathway of elongation of neuronal axons (also referred to as regeneration of neuronal axons) or impairing the function of a proteoglycan in an injured site.

In a spinal cord injury model, an intrathecal dosage per day of the improving agent of the present invention to a rat (body weight: 0.3 kg, amount of cerebrospinal fluid: 0.3 mL) is, in terms of chondroitinase ABC expressed in enzyme unit, from 0.03 mU to 30 mU, preferably from 0.3 mU to 10 mU, most preferably about 3 mU. When this dosage is converted into a dosage for a human adult (body weight: 60 kg, amount of cerebrospinal fluid: 150 mL) with the body weight and the amount of cerebrospinal fluid of the rat taken as 0.3 kg and 0.3 mL, respectively, the dosage for a human adult is about 200 times as much as that for the rat on the basis of the body weight, and about 500 times as much as that for the rat on the basis of the amount of cerebrospinal fluid in consideration of direct administration thereof into the dura mater. Accordingly, the dosage for a human adult (average body weight: 60 kg, average amount of cerebrospinal fluid: 150 mL) is as follows.

In the case of conversion on the basis of the body weight, the intrathecal dosage per day is from 6 mU to 6000 mU, preferably from 60 mU to 2000 mU, most preferably about 600 mU.

Further, in the case of conversion on the basis of the amount of cerebrospinal fluid, the intrathecal dosage per day is from 15 mU to 15000 mU, preferably from 150 mU to 5000 mU, most preferably about 1500 mU.

Therefore, in overall consideration of the above-mentioned conversion methods, the intrathecal dosage per day is from 6 mU to 15000 mU, preferably from 60 mU to 5000 mU, most preferably from about 600 mU to 1500 mU.

The duration of administration should be determined by a health care professional such as a medical doctor in consideration of the expression level of a chondroitin sulfate proteoglycan in an injured site and a possibility of occurrence of adverse reactions or the like and according to the symptoms, however, as a guide, in the case of continuous administration, it is up to about 8 weeks, preferably up to about 4 weeks, more preferably up to about 2 weeks after receiving an injury. The administration start time is preferably immediately after to about 3 days after receiving an injury.

Incidentally, in the case where chondroitinase ABC is used as the active ingredient, a preferred specific activity thereof is not less than about 300 U/mg protein, and therefore, the above-mentioned intrathecal dosage per day corresponds in terms of the weight of the enzyme protein as follows: 6 mU corresponds to about 0.02 µg or less, 15000 mU corresponds to about 50 µg or less, 60 mU corresponds to about 0.2 µg or less, 5000 mU corresponds to about 17 µg or less, and 600 mU corresponds to about 2 µg or less. Incidentally, 1 unit (1 U) of the enzyme amount (enzyme titer) of chondroitinase ABC is defined as an enzyme amount with which 1 µmol of unsaturated disaccharides is produced per minute when chondroitin sulfate C derived from shark cartilage is used as a substrate and reacted with the enzyme at pH 8.0 and 37° C. Incidentally, the dosage of "a lyase having an activity of degrading a chondroitin sulfate chain of a chondroitin sulfate proteoglycan" (the enzyme of the present invention) can also be determined by using the enzyme titer of each enzyme for the chondroitin sulfate proteoglycan which is a substrate as an index, and the range thereof is from 6 mU to 15000 mU in the same manner as chondroitinase ABC.

Incidentally, the amount or concentration of the enzyme per unit dosage form of the medicinal agent prepared using the improving agent of the present invention is determined according to the above-mentioned dosage. However, it is not necessary that the preparation have the amount or concentration of the enzyme when it is administered, and for example, immediately before or at the time of administration, the preparation may be diluted with a diluent to an effective and safe concentration. Accordingly, the present invention also provides a kit containing such a diluent and the above-mentioned medicinal agent of the present invention in combination.

The improving agent of the present invention is used for improving, curing, or preventing neuropathic pain due to a hyperalgesic response caused by an acute disorder or a chronic disorder in the central nervous system (CNS) including the spinal cord and brain or the peripheral nervous system, particularly allodynia and sensory nerve dysfunction. Examples of the disease causing neuropathic pain to which the improving agent of the present invention is effectively applied include central nervous disorders, specifically CNS injuries and diseases including spinal cord injuries, traumatic brain injuries, and the like can be exemplified as typical examples. However, the improving agent of the present invention can be effectively applied particularly to spinal cord injuries. The spinal cord injuries include diseases and traumatic injuries such as neuronal crush injuries caused by a traffic accident, a fall accident, a contused wound, a gunshot wound, and another injury. By administering the improving agent of the present invention, clinical improvement can be obtained in neuropathic pain due to a hyperalgesic response accompanying such a disease, particularly allodynia and sensory nerve dysfunction.

It is also possible to perform the treatment of neuropathic pain by using the medicinal agent prepared using the improving agent of the present invention in combination with another medicinal agent known to have an improving effect on neuropathic pain. Examples of such a medicinal agent include, as illustrated below, NSAIDs, opioids, and analgesic adjuvants. Examples of the opioid analgesic include morphine, fentanyl, oxycodone, codeine phosphate, pethidine, buprenorphine, tramadol, pentazocine, and butorphanol. Further, examples of the analgesic adjuvant include antidepressants such as a tricyclic type (such as amitriptyline or nortriptyline), a tetracyclic type (such as Tetramide), an SSRI (such as paroxetine or fluvoxamine), and an SNRI (milnacipran); anticonvulsants such as carbamazepine, lamotrigine, zonisamide, valproic acid, and clonazepam; antispasmodics such as baclofen; antiarrhythmics such as lidocaine and mexiletine; NMDA receptor antagonists such as ketamine, dextromethorphan, amantadine, and ifenprodil; and formulations containing an extract isolated from the inflamed skin of rabbits inoculated with a vaccinia virus such as Neurotropin. Further, gabapentin (an anticonvulsant) and pregabalin which are each a calcium channel blocker (bonding to an α2δ subunit) and have been receiving public attention recently can also be exemplified. It is also possible to use the present inventive medicinal agent in combination with a medicinal agent having an antiinflammatory activity, for example, a steroid agent such as methylprednisolone sodium succinate, dexamethasone, or betamethasone; or fasudil which is an Rho kinase inhibitor.

EXAMPLES

Hereinafter, the present invention will be described in detail with reference to Examples, however, the present invention should not be interpreted by limiting to the following description.

Example 1: Improving Activity of Chondroitinase ABC on Allodynia and Sensory Nerve Dysfunction Such as Hyperalgesia or the Like After Spinal Cord Injury (Experimental Method)

As animals, S.D. rats (Nippon SLC Co., Ltd., female, 9 weeks of age) were used. Under anesthesia with a cocktail of ether and ketamine, the ninth and the twelfth thoracic vertebrae were laminectomized, and a spinal cord injury on the ninth thoracic vertebra was induced by crushing using IH-0400 Impactor. After the injury, small incision was done to the dura mater of the twelfth thoracic vertebra and a microtube was inserted into the subarachnoid cavity under a microscope. The microtube was connected to an osmotic pump (Alzet Osmotic Pump) in which a test sample was previously filled. The tube and the pump were fixed onto the interspinal ligament and the muscle. Thereafter, the wound of the muscle layer and the skin was closed. After the operation, the rat was orally given an antibiotic for two weeks. The manipulative urination was performed once a day until micturition reflex was recovered. The test sample was continuously administered intrathecally for 14 days starting from immediately after the injury (administration rate: 12 μL/24 hours; total dose: 168 μL/14 days). As the test sample, the following two types were used.

(1) Chondroitinase ABC (0.05 U/200 μL, Seikagaku Corporation)
(2) Physiological saline (200 μL, control)

Incidentally, as the above-mentioned chondroitinase ABC, a solution prepared by dissolving a lyophilized product obtained by formulating a high-purity chondroitinase ABC (which shows a single band in gel electrophoresis (SDS-PAGE) and has a specific activity of 380 U/mg, and from which nucleic acids (DNAs) and proteases have been removed) derived from *Proteus vulgaris* described in Japanese Patent No. 3980657 and U.S. Pat. No. 6,184,023 into a preparation by the method described in U.S. Pat. No. 6,007,810 (a method using polyethylene glycol and saccharose) in physiological saline was used.

Experimental Results Part 1: Improving Effect on Mechanical Allodynia (Response to Pressure Stimulation: Touch Test)

Figure 1:
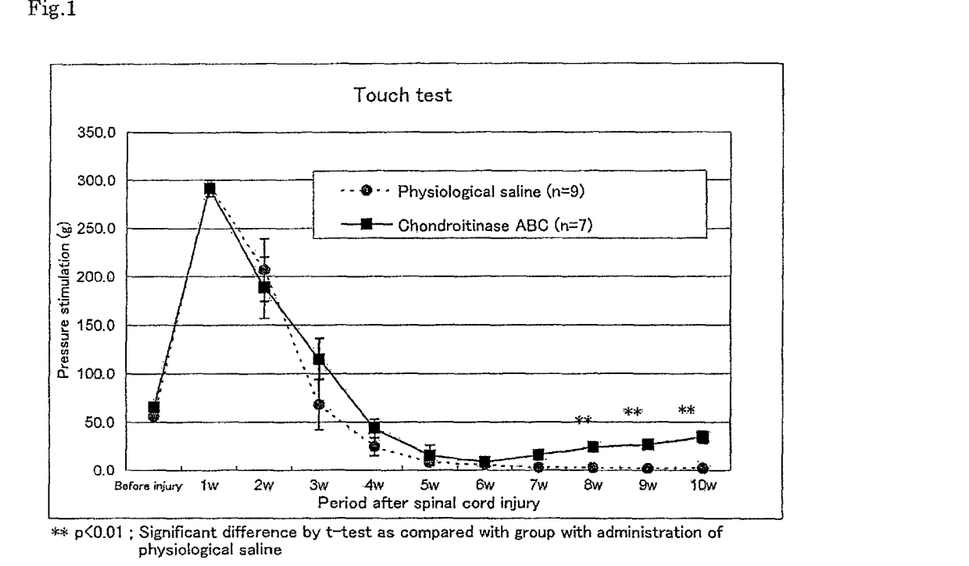
[FIG. 1] A graph showing an improving effect of chondroitinase ABC on mechanical allodynia in Example 1 (response to pressure stimulation: touch test).

Before the injury and once a week from one week after the injury to 10 weeks thereafter, each rat was placed in a small box and allowed to stand still for 15 minutes. When the rat became quiet, a stimulation was applied to the plantar surface of the hind limbs from the downside using von Frey filaments (several kinds of filaments of different stimulation intensities). By using an up-down method in which application of a strong stimulation and a weak stimulation was repeated to determine a correct stimulation threshold value (Chaplan, S. R., Bach, F. W., Pogrel, J. W., Chung, J. M., Yaksh, T. L., Quantitative assessment of tactile allodynia in the rat paw, J. Neurosci. Methods, 53, 55-63 (1994)), the pressure stimulation of the filament by which the rat felt pain and moved the hind limb was measured for each of the right and left hind limbs, and an average value was calculated and shown (unit: gram). The results of the cases where the two kinds of test samples were administered, respectively, are shown in FIG. 1. As is apparent from FIG. 1, in the group with the administration of physiological saline, the pressure stimulation of the filament showed a high value from one week to two weeks after the injury as compared with that before the injury, and an insensitive response to the stimulation applied to the hind limbs was observed. However, as from four weeks after the injury, the pressure stimulation of the filament showed a low value as compared with that before the injury and, after six weeks from the injury, a hypersensitive symptom in which a response was resulted even by a slight stimulation to the hind limb was observed. On the other hand, in the group with the administration of chondroitinase ABC, although a similar tendency to that in the case of the group with the administration of physiological saline was observed up to six weeks after the injury, however, after seven weeks from the injury, a hypersensitive response was gradually improved. After 10 weeks from the injury, the pressure stimulation of the filament showed a comparable level to that before the injury, and therefore, a remarkable improving (treating) effect on mechanical allodynia was observed in the administration group such that the sensory nerve function returned to a normal level.

Experimental Results Part 2: Evaluation of Sensory Nerve Function (Response to Thermal Stimulation: Tail Flick Test)

Figure 2:
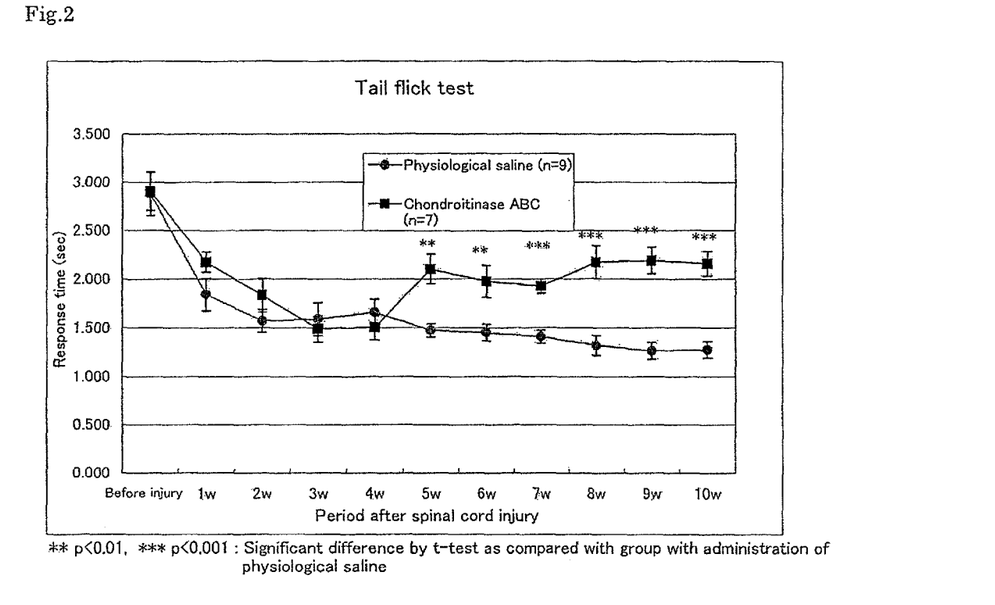
[FIG. 2] A graph showing an improving effect of chondroitinase ABC on thermal allodynia in Example 1 (response to thermal stimulation: tail flick test).

Before the injury and once a week from one week after the injury to 10 weeks thereafter, the tail of each rat was immersed in a bath of 55° C. and the time until the rat flicks the tail (response time) was measured (unit: second). The measurement was performed three times with an interval of 15 minutes and an average value was calculated and shown. The results of the cases where the two kinds of test samples were administered, respectively, are shown in FIG. 2. As is apparent from FIG. 2, in the group with the administration of physiological saline, the response time was reduced as the day went on after the injury as compared with that before the injury and a hypersensitive response to thermal stimulation was observed. On the other hand, in the group with the administration of chondroitinase ABC, although a similar tendency to that in the case of the group with the administration of physiological saline was observed in an early stage after the injury, however, the hypersensitive response to thermal stimulation was improved as from five weeks after the injury and, after eight weeks from the injury, the response time was stable and showed an almost comparable level to that before the injury, and therefore, a remarkable recovery (an improving (treating) effect on thermal allodynia) was observed in the administration group such that the sensory nerve function returned to a normal level.

Experimental Results Part 3: Somatosensory Evoked Potential

Figure 3:
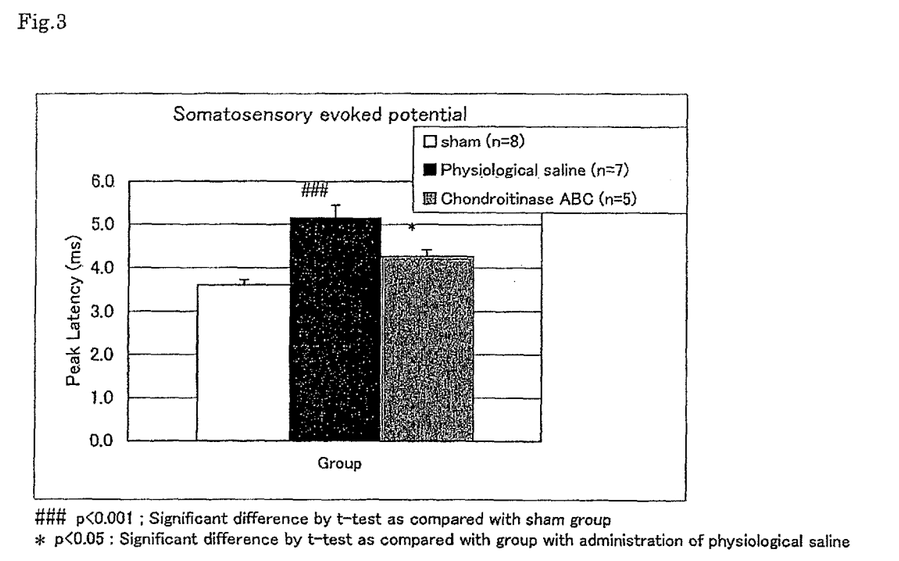
[FIG. 3] A graph showing a recovery activity of chondroitinase ABC on a sensory nerve in Example 1 (by somatosensory evoked potential (SEP) measurement).

A somatosensory evoked potential (SEP) was recorded on day 56 after the operation. Under anesthesia with ketamine hydrochloride, the wound made at the time of inducing the injury was opened and the dura mater on the rostral and caudal sides in the injured site of the spinal cord injury was exposed, and a stimulation electrode and a measurement electrode were placed on the dura mater on the caudal side and on the rostral side, respectively. Then, a stimulation was applied for a given period of time from the downside, and a potential transmitted to the upside was measured. A ground wire was placed between respective electrodes. The time from the stimulation to the first wave (latency) and the time from the stimulation to the second wave showing a clear wave peak (peak latency: PL) were measured (unit: millisecond (ms)). For both waves, 100 measurements were summed and averaged. The results of measured PL are shown in FIG. 3. As is apparent from FIG. 3, the group with the administration of chondroitinase ABC had a significant recovery activity on sensory nerve also from an electrophysiological standpoint.

Reference Example 1: Improving Activity of Chondroitinase ABC on Motor Dysfunction After Spinal Cord Injury (Experimental Method)

An experiment was performed in the same manner as in Example 1.

Reference Experimental Results Part 1: Evaluation of Hind Limb Motor Nerve Function (BBB Test)

Figure 4:
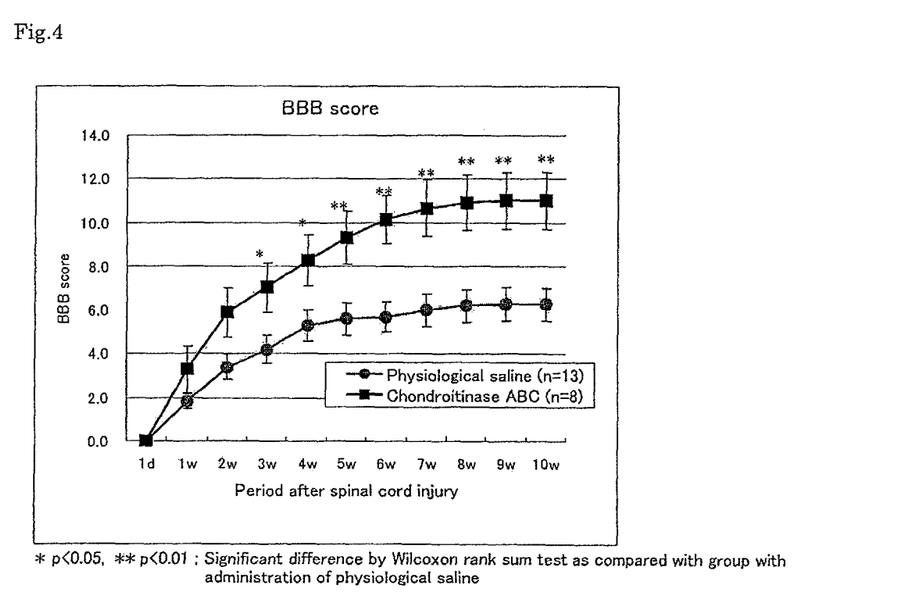
[FIG. 4] A graph showing the results of evaluation of a hind limb motor nerve function (BBB test) using chondroitinase ABC in Reference example 1.

One day after the injury and once a week from one week after the injury to 10 weeks thereafter, the hind limb motor nerve function was evaluated using a Basso-Beattie-Bresnahan (BBB) scale in accordance with a method of Basso et al. (Basso, D. M., Beattie, M. S. & Bresnahan, J. C., Graded histological and locomotor outcomes after spinal cord contusion using the NYU weight-drop device versus transection, Exp. Neurol., 139, 244-256 (1996)), and the results were expressed as BBB scores. The test was performed in a blind manner by two examiners and the score was expressed as an average value of the results of two examiners. As for the statistical analysis, intergroup comparisons for the respective evaluation time points were performed using a Wilcoxon rank sum test and determination was made with a P value of less than 5% considered significant. The results of the cases where the two kinds of test samples were administered, respectively, are shown in FIG. 4. As is apparent from FIG. 4, in the group with the administration of chondroitinase ABC, a significant recovery of the hind limb motor nerve function was observed as compared with the group with the administration of physiological saline.

Reference Experimental Results Part 2: Evaluation of Hind Limb Motor Nerve Function (Grid Test)

Figure 5:
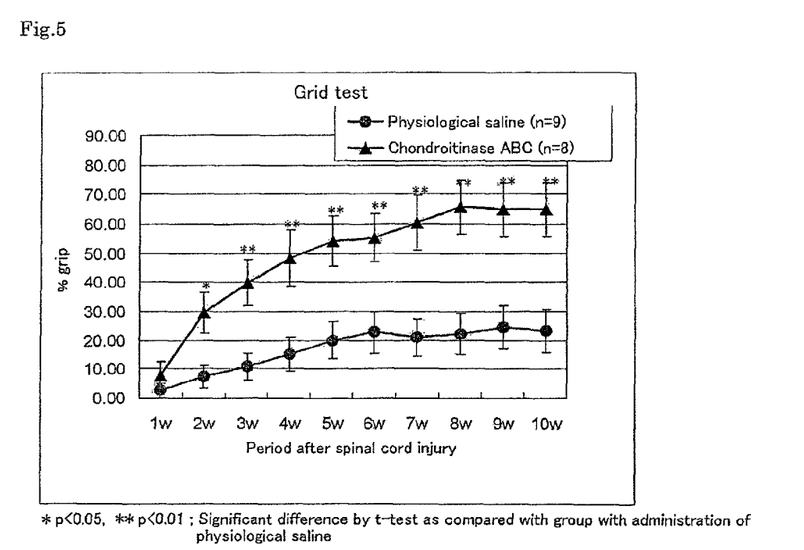
[FIG. 5] A graph showing the results of evaluation of a hind limb motor nerve function (grid test) using chondroitinase ABC in Reference example 1.

Once a week from one week after the injury to 10 weeks thereafter, each rat was placed on a net (grid) of 2 cm×2 cm and allowed to walk thereon for three minutes, and the number of times that the rat could grip the grid with the hind limb and the total number of steps were measured. The ratio of the number of times that the rat could grip the grid to the total number of steps was defined as a % grip value and an average value was calculated for each of the right and left hind limbs and shown. As for the statistical analysis, intergroup comparisons for the respective evaluation time points were performed using a t-test and determination was made with a P value of less than 5% considered significant. The results of the cases where two kinds of test samples were administered, respectively, are shown in FIG. 5. As is apparent from FIG. 5, in the group with the administration of chondroitinase ABC, a significant recovery of the hind limb motor nerve function was observed as compared with the group with the administration of physiological saline.

Reference Experimental Results Part 3: Evaluation of Hind Limb Motor Nerve Function (Footprint Test)

Figure 6:
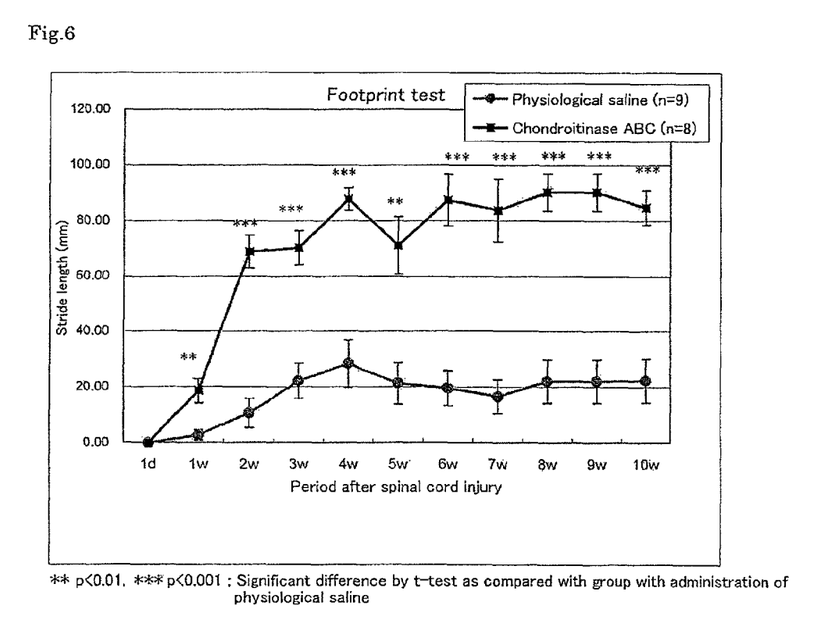
[FIG. 6] A graph showing the results of evaluation of a hind limb motor nerve function (footprint test) using chondroitinase ABC in Reference example 1.

One day after the injury and once a week from one week after the injury to 10 weeks thereafter, ink was applied to the hind limbs of each rat and the rat was allowed to walk on a sheet of paper with a size of 50 cm, whereby footprints of the hind limbs were obtained. The stride length was measured for each of the right and left hind limbs from the footprints of the hind limbs on the paper, and an average value was calculated and shown (unit: mm). As for the statistical analysis, intergroup comparisons for the respective evaluation time points were performed using a t-test and determination was made with a P value of less than 5% considered significant. The results of the cases where the two kinds of test samples were administered, respectively, are shown in FIG. 6. As is apparent from FIG. 6, in the group with the administration of chondroitinase ABC, a significant recovery of the hind limb motor nerve function was observed as compared with the group with the administration of physiological saline.

Reference Experimental Results Part 4: Motor Nerve Evoked Potential

Figure 7:
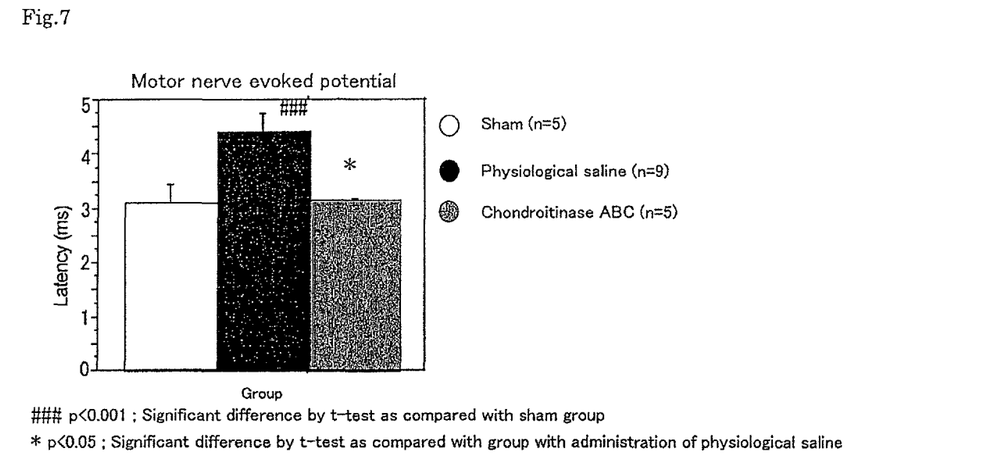
[FIG. 7] A graph showing a recovery activity of chondroitinase ABC on a motor nerve in Reference example 1 (by motor nerve evoked potential (MEP) measurement).

A motor nerve evoked potential (MEP) was recorded on day 56 after the operation. Under anesthesia with ketamine hydrochloride, the wound made at the time of inducing the injury was opened and the dura mater on the rostral side in the injured site of the spinal cord injury was exposed, and a stimulation electrode was placed on the dura mater on the rostral side. As recording electrodes for both hind limbs, two needle electrodes were placed on each of the right and left gastrocnemius muscles at an equal interval. Then, a stimulation was applied for a given period of time, and a potential transmitted to each of the right and left hind limbs was measured. A ground wire was placed between respective electrodes. The time from the stimulation until a wave form was recorded (latency: L) and the time from the appearance of the wave form to the disappearance thereof (duration) were measured (unit: millisecond (ms)). For both waves, 50 measurements were summed and averaged for each results of the right and left hind limbs. The results of measured L are shown in FIG. 7. As is apparent from FIG. 7, the group with the administration of chondroitinase ABC had a significant recovery activity on motor nerve also from an electrophysiological standpoint.

Preparation Example 1:

A solution preparation containing the above-mentioned high-purity chondroitinase ABC at a concentration of 0.05 U/200 μL was prepared by dissolving the chondroitinase ABC in physiological saline.

INDUSTRIAL APPLICABILITY

The present invention has industrial applicability in the point that an improving agent for neuropathic pain caused by a nervous disorder, particularly a therapeutic agent for allodynia and sensory dysfunction, containing, as an active ingredient, a lyase which has an activity of degrading a chondroitin sulfate chain of a chondroitin sulfate proteoglycan, and is typified by chondroitinase ABC which selectively removes a chondroitin sulfate side chain and a dermatan sulfate side chain forming side chains of a proteoglycan can be provided.

The invention claimed is:

1. A method for treating neuropathic pain due to a hyperalgesic response, comprising the step of:
   administering to a patient having a neuropathic pain due to a hyperalgesic response, a lyase having an activity of degrading a chondroitin sulfate chain of a chondroitin sulfate proteoglycan.

2. The method of claim 1, wherein the lyase is chondroitinase ABC.

3. The method of claim 1, wherein the patient has allodynia.

4. The method of claim 1, wherein the neuropathic pain is caused by a central nervous disorder.

5. The method of claim 1, wherein the neuropathic pain is caused by a spinal cord injury.

6. The method of claim 1, wherein:
   the patient has a neuropathic pain caused by a nerve injury; and
   the lyase is continuously administered to the site of the neuropathic pain.

7. The method of claim 6, wherein the lyase is administered intrathecally to the subarachnoid cavity.

8. The method of claim 6, wherein the lyase is continuously administered starting from immediately to 3 days after the injury, for a period of up to 8 weeks.

9. The method of claim 6, wherein the step of administering the lyase comprises administering a parenteral preparation of the lyase.

10. The method of claim 6, wherein the lyase is administered intrathecally at 6 to 15000 mU per day per 60 kg body weight.

11. The method of claim 6, wherein the lyase is administered intrathecally at 60 to 5000 mU per day per 60 kg body weight.

12. The method of claim 6, wherein the lyase is administered intrathecally at 600 to 1500 mU per day per 60 kg body weight.

* * * * *